United States Patent [19]
Stevens et al.

[11] Patent Number: 5,512,056
[45] Date of Patent: Apr. 30, 1996

[54] COMPRESS AND METHOD

[76] Inventors: Robert R. Stevens, 13500 SW. 63rd Ave., Miami, Fla. 33156; Rene Guerra, 2732 W. 54th St., Hialeah, Fla. 33016

[21] Appl. No.: 305,133

[22] Filed: Sep. 13, 1994

[51] Int. Cl.⁶ ..................... A61B 17/12
[52] U.S. Cl. ........................ 606/203
[58] Field of Search ............ 606/201–204

[56] References Cited

U.S. PATENT DOCUMENTS

| | | | |
|---|---|---|---|
| 37,156 | 12/1862 | Dunton | 606/203 |
| 1,281,653 | 10/1918 | Plummer | 606/203 |
| 4,182,338 | 1/1980 | Stanulis | 606/203 |
| 4,997,438 | 3/1991 | Nipper | 606/204 |
| 5,263,965 | 11/1993 | Roth | 606/201 |

FOREIGN PATENT DOCUMENTS

| | | | |
|---|---|---|---|
| 0462088 | 12/1991 | European Pat. Off. | 606/201 |
| 0021060 | of 1914 | United Kingdom | 606/203 |

*Primary Examiner*—Stephen C. Pellegrino
*Assistant Examiner*—William W. Lewis
*Attorney, Agent, or Firm*—Jack E. Dominik

[57] ABSTRACT

The discovery that by use of a spreader beam and pressure pad which has an adjustable strap secured to its ends, and then positioning the spreader beam with the pressure pad over the wound or puncture, will inhibit the bleeding and enhance coagulation is disclosed. As a result of the method, substantially less than 180° radially of a limb or a body portion is subject to the pressure of the strap. Only a small portion of the radius of the skin is engaged by the pressure pad itself. The method of the invention derives from utilizing a spreader beam and pressure point with a strap at each end of the spreader beam in surrounding engagement with a limb or other body portion which has been punctured, and then positioning the pressure pad to apply pressure to the puncture point, and keeping the compress in place until the wound has ceased bleeding.

8 Claims, 1 Drawing Sheet

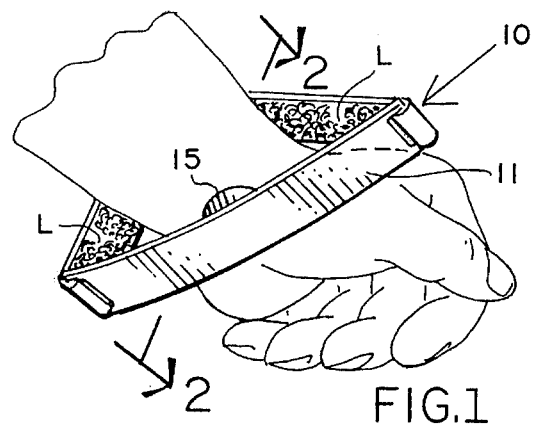
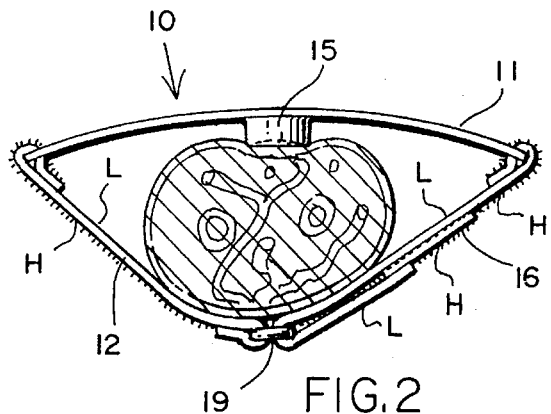
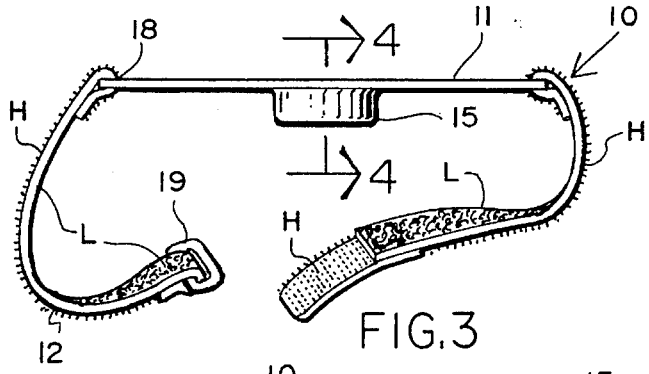
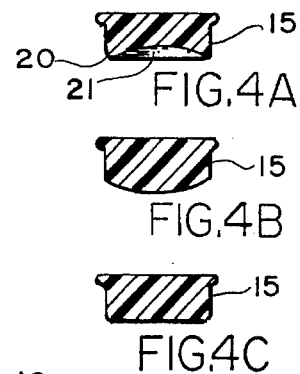
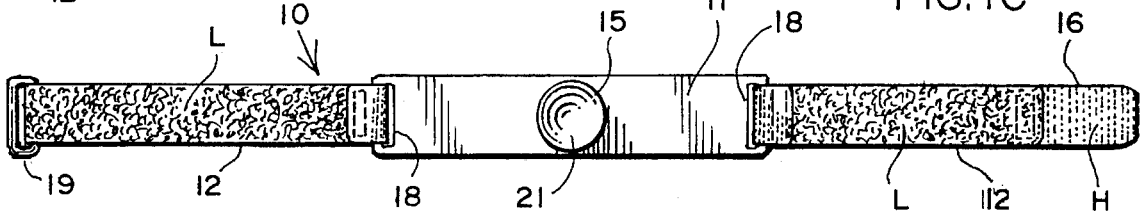
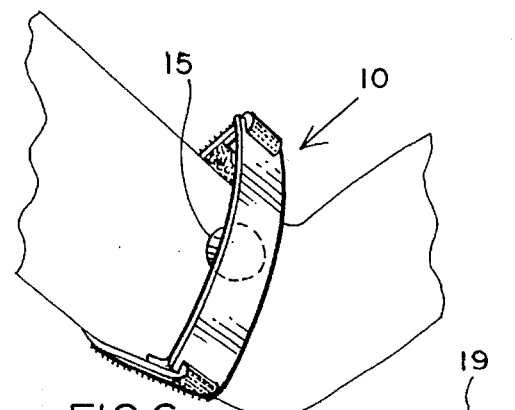
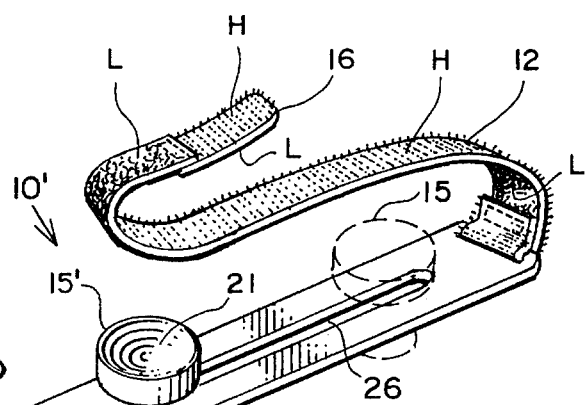

COMPRESS AND METHOD

FIELD OF THE INVENTION

The present invention finds particular utility in applying compression to a point of puncture on the skin. Compression is typically applied when removing a needle from a point of vascular access, post-hemodialysis, catheterization, or intravenous feeding to mention a few.

SUMMARY OF THE PRIOR ART

The prior art is exemplified by U.S. Pat. Nos. 5,269,803; 4,308,861; 4,273,130; 4,182,338; 3,586,001; 3,570,496; and 38,442. Basically the prior art as just identified is directed to various techniques for applying pressure such as hemostasis pressure pad bands, dialysis clamps, and constrictors. The bulk of the prior-art patents and devices and methods exemplified suffer from the entire encirculation of the particular limb involved. As such, they accomplish a tourniquet effect which constricts the flow of blood in the limb to which the appliance has been applied. Accordingly, it is highly desirable to provide for localized compression at the point of puncture when a hypodermic needle or catheter is being withdraw. This allows the blood to coagulate and therefore close the puncture. Such application should be without total pressure which would otherwise constrict the limb, reduce blood flow, and otherwise induce discomfort in the patient.

SUMMARY OF THE INVENTION

The present invention derives from the discovery that by use of a spreader beam and pressure pad which has an adjustable strap secured to its ends, and then positioning the spreader beam with the pressure pad over the wound or puncture, will inhibit the bleeding and enhance coagulation. As a result of the method, substantially less than 180° radially of a limb or a body portion is subject to the pressure of the strap. Only a small portion of the radius of the skin is engaged by the pressure pad itself. The method of the invention derives from utilizing a spreader beam and pressure point with a strap at each end of the spreader beam in surrounding engagement with a limb or other body portion which has been punctured, and then positioning the pressure pad to apply pressure to the puncture point, and keeping the compress in place until the wound has ceased bleeding.

In view of the foregoing it is a principal object of the present invention to provide a compress which will encircle a limb or body portion, compress a small portion of the skin, subcutaneous tissue, and vessel directly below the compress, and yet permit unconstricted blood flow throughout a major portion of the limb or body portion while the blood coagulation takes place.

Yet another object of the present invention is to provide a compress which can be adjusted to a wide variety of limb or body portion sizes and limb positions varying from as small as the wrist to as large as the thigh, groin area, or the torso.

Another object of the present invention looks to a construction of a compress which inherently inhibits its use in an overly constricting fashion on a limb or body portion.

BRIEF DESCRIPTION OF THE ILLUSTRATIVE DRAWINGS

Further objects and advantages of the present invention will become apparent as the following description of an illustrative embodiment proceeds, taken in conjunction with the accompanying drawings, in which:

FIG. 1 is a perspective partially diagrammatic view of the subject compress applied to the wrist of a patient;

FIG. 2 is a transverse sectional view of the limb of FIG. 1 showing diagrammatically how the compress engages the limb;

FIG. 3 is a front elevation of the subject compress illustrating the spreader beam, pressure pad, and strap;

FIG. 4A is a transverse sectional view taken through the pressure pad of FIG. 3 essentially on section lines 4—4 of FIG. 3 and in enlarged scale and showing a concave lower shape;

FIG. 4B is a comparable section but taken through a pressure pad in which there is a concave shape at the skin engaging point as distinguished from the convex shape in FIG. 4A;

FIG. 4C is yet another embodiment of the pressure pad showing an essentially square or flat bottom. Whether square or rectangular or triangular, the bottom shown in FIG. 4C is relatively flat;

FIG. 5 is yet another view of the compress but showing the two strap portions fully extended along with the method for adjusting the strap to varying lengths as dictated by varying sized limbs or body portions to which the compress is affixed;

FIG. 6 is yet another view of the subject compress but applied to a typical arm of a patient immediately above the elbow, encircling a puncture which typically is taken during the course of blood tests, withdrawing blood, and the like; and FIG. 7 shows a modified embodiment in which the press pad can be adjusted along the spreader beam.

DESCRIPTION OF A PREFERRED EMBODIMENT

The compress 10 of the subject invention is shown in a typical operable relationship to the wrist of a patient as identified in FIG. 1. The compress 10, as particularly noted in FIGS. 2 and 3, includes a spreader beam 11 at the ends of which is a strap 12, but the strap 12 is adjustable by means of a buckle 16, and loop 19 and is desirably a non-extendable or inelastic strap.

The pressure pad 15 which is shown in FIG. 4A has a rim 20 at its lower portion and a concave recess 21 interiorly of the rim 20. While the rim 20 is shown as being circular, and the recess 21 is convex, it will be appreciated that various other configurations of the pressure pad 15 may be applicable, including squares, triangles, hexagonal sections, oval sections, convex or flat section as exemplified in FIGS. 4B and 4C and combinations of all of the above. What is important, however, is that the pressure pad 15 be substantially totally circumambient to the puncture point so that the pressure which is applied will be applied as uniformly as possible in surrounding relationship to the puncture point or wound.

In operation it is anticipated that a pad of gauze, or a thin film of membrane or releasable non-stick liner will be placed over the puncture point. The operator then takes the compress 10 and when possible sights through the transparent material in order to locate the center of the rim 20 or press over the puncture point in the skin of the patient. Once the unit is applied, it is retained in position by adjusting the strap 12 until a coagulation of the blood is observed by the attendant.

Typically the subject unit varies in length from one end of the spreader beam 11 to the other. The slots 18 may be of varying dimensions, just so that they receive the ends of the strap 12 in secured encircling relationship. The materials that are used are not critical to the invention, but a polycarbonate is desirably used for molding the spreader beam 11 and the pressure pad 15. Such a polycarbonate is not only sterilizable, but desirably transparent which permits visual inspection of the positioning and the coagulation of the blood of the patient.

It will be appreciated that the present invention may also be applied to other portions of the body. For example, a puncture in the chest with a modest chest wound may result in air passing in and out of the chest cavity. By applying the subject compress 10 to the chest, this activity can be inhibited while the patient seeks further treatment.

The method of the present invention contemplates the use of a compress 10 which has a pressure pad 15, and in which the compress includes a spreader beam 11 which may flex as it is secured by means of an adjustable strap such as illustrated by reference numeral 12. The pressure pad 15 is oriented substantially over the puncture point and in circumambient relationship to the puncture point so that the pad will press down on the epidermis or skin of the patient in a relatively uniform manner, even though there may be a pad of gauze or a thin film of membrane or releasable liner between the rim and the skin. The strap buckle 16 is passed through the loop 19, pulled snugly, and the Velcro members are formed. The most important discipline to be followed in utilizing the subject invention is to make sure that an adjustable pressure can be applied to the pressure pad, and yet desirably less than 180° of a limb or a body portion be engaged by the strap 12. To this end the strap 12 may have an extendable elastic portion, and the spreader beam 11 be relatively inflexible. Alternatively the adjustable strap 12 may be non-stretchable, but the spreader beam 11 flexible to provide for the compression. In a less desirable form, the tightening of the strap itself will bring about the pressure, but not with the effectiveness that either an extendable strap, flexible spreader beam, or any combination thereof will achieve.

While materials and dimensions are not necessarily critical to the invention, the same will be identified as desirable in a commercial unit. For example, the spreader beam 11 is formed of polycarbonate, with a thickness of one-eighth to one-quarter inches, a width of one to two inches, and a length of six to twenty inches in the embodiment illustrated in FIGS. 1–6. The strap with the buckle portion is at least 25% longer than the spreader. Illustrated as H for hook and L for loop are the opposed faces of the Velcro-type material utilized for securing. As to the alternative embodiment compress 10' shown in FIG. 7, the polycarbonate material for the beam 11' remains the same. The length, however, is longer, with the width remaining at about the same. The control knob 25 adjustably secures the pressure pad 15 along the control slot 26. With the longer embodiment such as illustrated in FIG. 7 of the compress 10' application of the pressure pad 15' can ideally be done in the groin area after a typical angioplasty procedure has been performed on the patient. Otherwise the basic elements of the compress 10' remain essentially the same, all common elements being identified by the "prime" after the reference numerals.

It will be understood that various changes in the details, materials and arrangements of parts which have been herein described and illustrated in order to explain the nature of the invention, may be made by those skilled in the art within the principle and scope of the invention as expressed in the appended claims.

What is claimed is:

1. A compress comprising, in combination a single spreader beam having two ends, said single beam being formed from flexible material a single pressure pad, having a longitudinal dimension measured along the length of the beam, secured at an intermediate point between the ends of the single spreader beam and extending downwardly, said beam ends being positioned substantially twice the longitudinal dimension of the pressure pad from the pressured pad, and a strap secured to both ends of the subject spreader beam which adjustably surrounds a body portion of a patient and causes the spreader beam to hold the pressure pad in compressed relationship to a puncture of the skin while at the same time limiting the pressure of the strap to less than total encirclement of the body portion.

2. In the compress of claim 1 above, said pressure pad and spreader beam puncture being sufficiently transparent to view a bleeding point on the patient.

3. In the compress of claim 1 above, said spreader beam being sufficiently flexible to apply adjustable force on the pressure pad when the strap is shortened.

4. In the compress of claim 1 above, means for adjustably securing the pressure pad to the spreader beam along the length of the spreader beam, whereby the orientation of the pressure pad to the patient can be adjusted independently of the securement of the strap.

5. In the compress of claim 1 above, wherein said pressure pad is substantially circular and has a rim, the central portion interiorly of which is concave.

6. In the compress of claim 1 above, wherein said pressure pad has a substantially convex lower portion.

7. In the compress of claim 1 above, wherein said pressure pad has an essentially flat bottom surface.

8. In the compress of claim 1 above, wherein said pressure pad is formed with a peripheral portion which permits the pad to take up a circumambient relationship to the puncture of the skin engaged with the pressure pad.

* * * * *